(12) United States Patent
Chung et al.

(10) Patent No.: US 9,163,210 B2
(45) Date of Patent: Oct. 20, 2015

(54) METHOD OF DOUBLE-COATING LACTIC ACID BACTERIA

(71) Applicant: Myung-Jun Chung, Seoul (KR)

(72) Inventors: Myung-Jun Chung, Seoul (KR); Young-Chai Cho, Kimpo-shi (KR); Soo-Dong Kim, Seoul (KR); Un-Pyoe Hong, Kimpo-shi (KR)

(73) Assignee: Myung-Jun Chung, Seoul (KR)

( * ) Notice: Subject to any disclaimer, the term of this patent is extended or adjusted under 35 U.S.C. 154(b) by 0 days.

(21) Appl. No.: 14/621,258

(22) Filed: Feb. 12, 2015

(65) Prior Publication Data

US 2015/0152378 A1  Jun. 4, 2015

Related U.S. Application Data

(63) Continuation of application No. 14/505,425, filed on Oct. 2, 2014, which is a continuation of application No. 10/456,513, filed on Jun. 6, 2003, now abandoned.

(51) Int. Cl.

| | |
|---|---|
| C12N 1/20 | (2006.01) |
| A61K 9/16 | (2006.01) |
| A23L 1/30 | (2006.01) |
| A61K 35/74 | (2015.01) |
| A23L 1/00 | (2006.01) |
| A61K 9/50 | (2006.01) |
| A61K 35/744 | (2015.01) |
| A61K 35/745 | (2015.01) |
| A61K 35/747 | (2015.01) |
| C12N 1/04 | (2006.01) |
| A61K 9/19 | (2006.01) |

(52) U.S. Cl.
CPC .............. *C12N 1/20* (2013.01); *A23L 1/0029* (2013.01); *A23L 1/3014* (2013.01); *A61K 9/1652* (2013.01); *A61K 9/1658* (2013.01); *A61K 9/1682* (2013.01); *A61K 9/19* (2013.01); *A61K 9/5015* (2013.01); *A61K 9/5036* (2013.01); *A61K 35/744* (2013.01); *A61K 35/745* (2013.01); *A61K 35/747* (2013.01); *C12N 1/04* (2013.01); *A23V 2002/00* (2013.01); *A23Y 2220/03* (2013.01); *A23Y 2240/75* (2013.01); *A23Y 2300/55* (2013.01); *C12N 2500/34* (2013.01); *C12N 2501/734* (2013.01); *C12N 2501/90* (2013.01); *C12N 2523/00* (2013.01)

(58) Field of Classification Search
None
See application file for complete search history.

(56) References Cited

U.S. PATENT DOCUMENTS

| | | |
|---|---|---|
| 3,677,897 A | 7/1972 | Jeffreys |
| 3,897,307 A | 7/1975 | Porubcan et al. |
| 4,205,132 A | 5/1980 | Sandine et al. |
| 4,956,185 A | 9/1990 | Cajigas |
| 5,466,463 A | 11/1995 | Ford |
| 5,637,494 A | 6/1997 | King |
| 6,214,585 B1 | 4/2001 | Kwon et al. |
| 6,365,148 B1 | 4/2002 | Kim et al. |
| 6,447,823 B1 | 9/2002 | Shin et al. |

FOREIGN PATENT DOCUMENTS

| | | |
|---|---|---|
| EP | 0285979 A2 | 10/1988 |
| JP | 2002-320473 A | 11/2002 |

OTHER PUBLICATIONS

Larisch et al., J. Microencapsulation, 1994, vol. 11, pp. 189-195.
http://www.usbio.net/technicalSheet.php?prodSku-E2245 (Elliker Broth) accessed Feb. 12, 2009.
Atlas et al., Microbiological Media, 1993, CRC, p. 949.

*Primary Examiner* — Blaine Lankford, Jr.
*Assistant Examiner* — David Berke-Schlessel
(74) *Attorney, Agent, or Firm* — Knobbe Martens Olson & Bear LLP

(57) ABSTRACT

The present disclosure relates to production of double-coated lactic acid bacteria using peptides and polysaccharide. Double-coated lactic acid bacteria show improved heat-resistance, acid-resistance, bile-resistance, storage stability and excellent survival rate when reaching intestine.

12 Claims, 4 Drawing Sheets

METHOD OF DOUBLE-COATING LACTIC ACID BACTERIA

RELATED APPLICATIONS

This is a continuation application of U.S. patent application Ser. No. 14/505,425, filed Oct. 2, 2014, which is a continuation application of U.S. patent application Ser. No. 10/456,513, filed Jun. 6, 2003. The disclosures of the parent applications are incorporated herein by reference in their entirety.

BACKGROUND

1. Field

The present disclosure relates to coating lactic acid bacteria with peptides and polysaccharide and the product by the same.

2. Discussion of Related Technology

It is well known that lactic acid bacteria has many physiological effects in improving and activating the functions of the intestines thereby maintaining good health. Non-coated lactic acid bacteria powder can be obtained by cultivating lactic acid bacteria, concentrating the culture and lyophilizing the concentrated culture. The non-coated lactic acid bacteria powders, however, are vulnerable to air, moisture and/or temperature. Therefore, when the lactic acid bacteria passes through the stomach after ingestion, almost all the lactic acid bacteria is killed by the gastric juice before reaching the intestine. Also, the non-coated culture powder has difficulty in maintaining stability during storage, distribution and processing for secondary products.

In order to overcome such problems, proposed have been a method for coating the lactic acid bacteria and a micro-encapsulation process using gelatins, sugars, gums, etc. The conventional process for coating the lactic acid bacteria usually comprises the step of introducing a specified coating material to the dried lactic acid bacteria culture as shown in FIG. 1. The lactic acid bacteria is cultivated M1, M2 within an anaerobic fermentation apparatus (herein after a "fermenter") using a fermentation medium containing peptones, meat extracts, yeast extracts, glucose and inorganic ions. Such components contained in the medium are water-soluble and used only for proliferation of the lactic acid bacteria.

The concentrated cultures M3 are obtained by means of centrifugal separation or ultra-filtration, the purpose of which is solely separation and concentration of the cultures. During deep freezing and lyophilization processes M4, a cryoprotectant is generally added to prevent the lactic acid bacteria from being killed. In turn, a coating composition in an aqueous solution MS is applied to the obtained lactic acid bacteria culture, followed by lyophilization. Alternatively, a microspherical bead type coating composition may be applied to the dried lactic acid bacteria culture, followed by a nozzle-injection in a micro-encapsulation process. Such conventional processes for coating the lactic acid bacteria include the steps for introduction of the coating composition or micro-encapsulation after concentrating and drying the cultures, which requires an expensive coating agent and additional steps thereby increasing production costs. Furthermore, materials and individual steps may overlap since the lyophilization process after coating it un a liquid state requires a cryoprotectant and a stabilizer to ensure improved viability and stability.

SUMMARY

One aspect of the present invention provides a process for preparing a double-coated lactic acid bacteria culture powder using protein and polysaccharide.

Another aspect of the present invention provides a lactic acid bacteria culture powder having enhanced moisture resistance, heat-resistance, acid-resistance and bile acid-resistance thereby improving stability by a cost-effective and simple process.

In accordance with one embodiment, there is provided a process for preparing a double-coated lactic acid bacteria powder comprising the steps of: preparing a protein aqueous solution; adding a proteolytic enzyme solution to the protein aqueous solution for proteolysis; cultivating a lactic acid bacteria using the protein aqueous solution; concentrating the lactic acid bacteria culture using a centrifuge wherein the lactic acid bacteria culture is coated with the protein; introducing the lactic acid bacteria culture into a polysaccharide aqueous solution and mixing it to form a homogenized solution; and lyophilizing the homogenized solution.

DETAILED DESCRIPTION OF EMBODIMENTS

Preferred embodiments of the process for preparing double-coated lactic acid bacteria culture powders according to the present invention using the protein and the polysaccharide will now be described below with reference to FIGS. 2 and 3.

Figure 1:
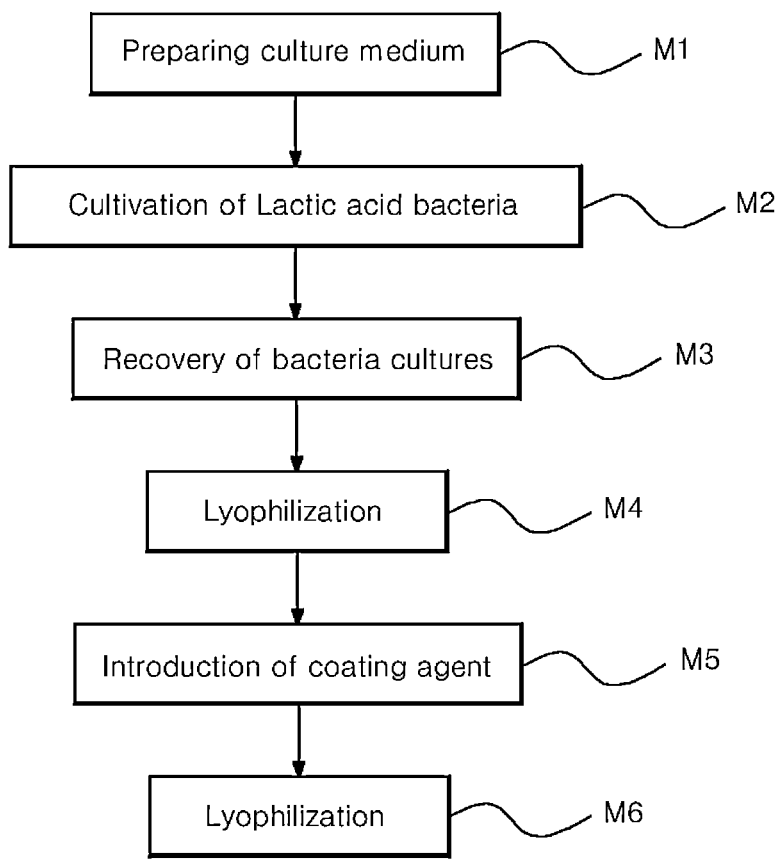
FIG. 1 is a flow chart showing a conventional process for preparing a coated lactic acid bacteria culture.
Figure 2:
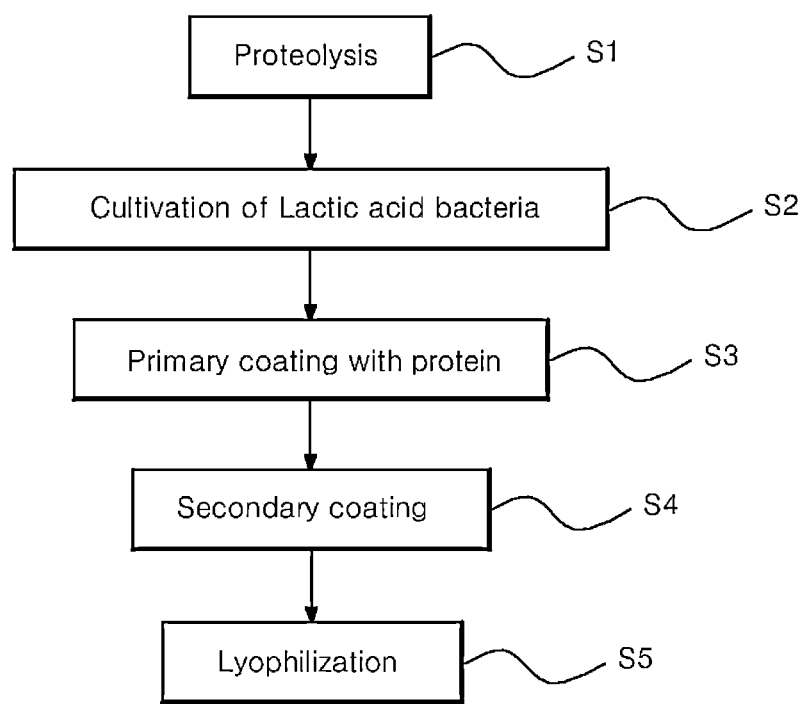
FIG. 2 is a flow chart showing a preferred embodiment according to the present invention.

FIG. 2 provides a flow chart showing an embodiment of the process for preparing the double-coated lactic acid bacteria powder, wherein a concentrated bacteria culture is double-coated with protein and polysaccharides and followed by a lyophilization process of the resultant double-coated bacteria culture to be in freeze dried powder form.

Figure 3:
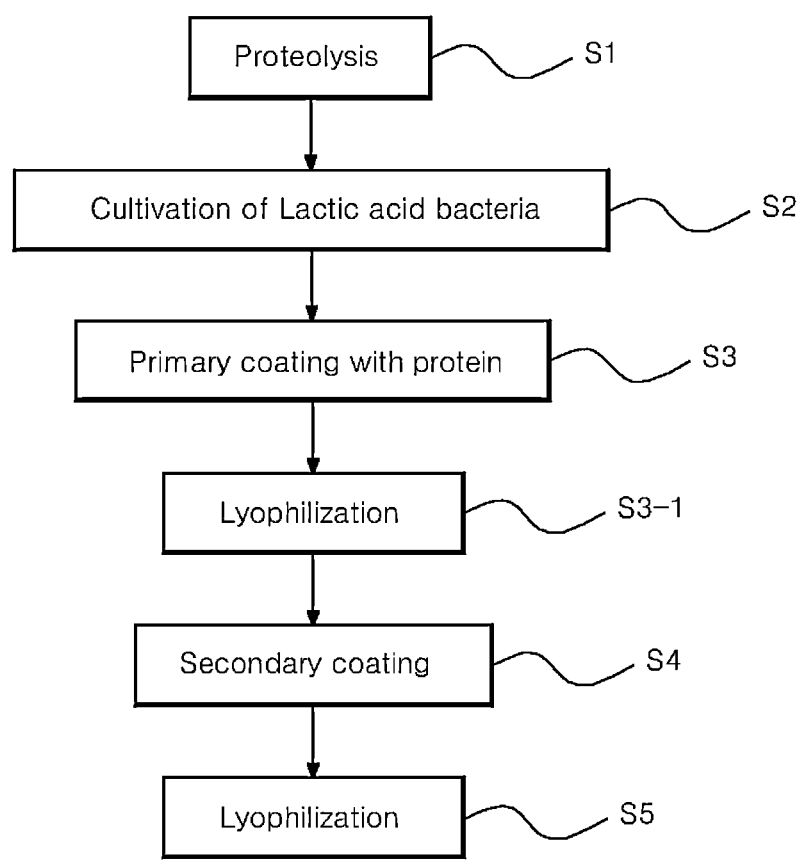
FIG. 3 is a flow chart showing another preferred embodiment according to the present invention.
Figure 4A:
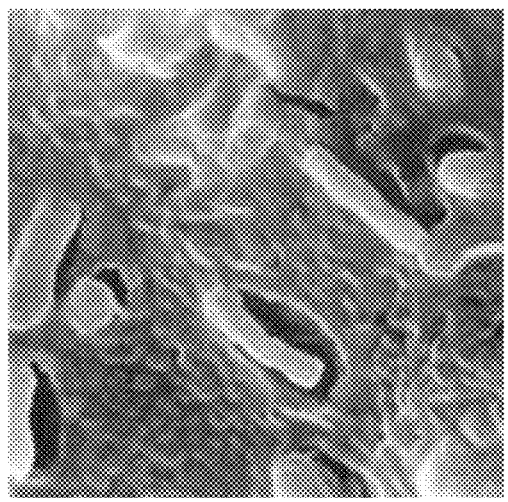
FIGS. 4A and 4B are pictures of double-coated lactic acid bacteria culture powders.
Figure 4B:
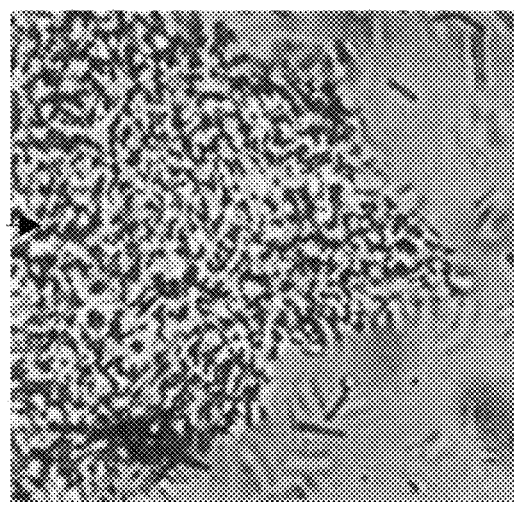

FIG. 3 illustrates a flow chart for another embodiment of the process for preparing the double-coated lactic acid bacteria powder including the steps of primarily coating lactic acid bacteria culture with protein followed by lyophilization, secondly coating the dried cultures with a polysaccharide solution, and finally lyophilizing the resultant double-coated culture.

According to the present invention, the process for producing the double-coated lactic acid bacteria culture powder comprises several steps including the proteolysis process of the protein solution, fermentation process of the lactic acid bacteria, the primary-coating process with a protein using a centrifuge and the secondary-coating process with a polysaccharide.

In the proteolysis step S1, 1 to 10% by weight of protein aqueous solution including skim milk and/or isolated soybean protein is prepared. A proteolytic enzyme solution is added, in amount of 0.01-1% by weight based on the total weight of the protein, to the protein aqueous solution for proteolysis.

The hydrolyzed products obtained after the proteolysis step can be classified as water-soluble or low molecular weight peptide components for cultivation of lactic acid bacteria and water-semisoluble or high molecular weight peptide components for the coating of a lactic acid bacteria culture.

For the fermentation (cultivation) step S2, there are added and dissolved 1-5% by weight of glucose, 0.1-1.5% by weight of yeast extract, 0.1-1.5% by weight of concentrated meat extract, 0.01-0.1% by weight of ionic components, such as ammonium citrate, sodium acetate, dipotassium phosphate, magnesium sulfate, manganese sulfate, sodium chloride and mixtures thereof, into the hydrolyzed protein solution.

Then, the lactic acid bacteria is cultivated, after steam-sterilization, in the solution containing protein and other mixtures within an anaerobic fermenter.

In the protein-coatings step 83, the lactic acid bacteria culture is separated and concentrated by using a high speed centrifuge at 15,000 RPM or more. A coating mechanism occurs during the centrifuge process, wherein residual protein components in the fermented solution are deposited with the bacteria culture, capturing and enclosing them.

The hydrolyzed product composition allows proliferation of the lactic acid bacteria, and conditions can be optimized by increasing or reducing the concentration of protein and enzyme considering the physiological properties of the used lactic acid bacteria. The hydrolyzed product can also function as cryoprotectants because it encloses the cultures thereby protecting the bacteria cultures from forming ice-crystals in a deep freezing process.

For the polysaccharide-coating step 84, prepared are a 1-10% by weight of polysaccharide aqueous solution including 1-10% by weight of xanthan gum, cellulose, levan and/or mixtures thereof, and a 35-45% by weight of cryoprotectant aqueous solution including 1-10% by weight of trehalose, malto-dextrin, mannitol and a skim milk, the weight of which is based on the total weight of the concentrated protein-coated bacteria cultures.

After sterilization under pressure, both of the above solutions are mixed together with the protein-coated bacteria cultures by agitating the mixtures in a stirrer to form a homogenized solution and then, freeze-dried.

Alternatively, a freeze-dried bacteria culture powder, which is coated with protein and lyophilized (83-1), may be mixed into the mixture of the above polysaccharide and cryoprotectant aqueous solution homogeneously using a stirrer and then, freeze-dried whereby the bacteria culture is secondly coated with polysaccharide.

During the lyophilization process, the lactic acid bacteria cultures homogenized in the polysaccharide solution adhere to each other having an excessively dense structure due to the strong adhesiveness of the polysaccharide among cultures. The lactic acid bacteria culture powders have a constant particle size ranging from 40-120 through grinding process.

With regard to properties of the polysaccharide used as the secondary coating agent in the present invention, the polysaccharide has an inherent adhesiveness and its hydrophilic properties allow it to be compatible with the primary coating agent, that is, the protein, as well as other water-soluble sugars, cryoprotectants including amino acid and stabilizers for lactic acid bacteria. In particular, the polysaccharide in an aqueous solution has extremely low solubility under acidic conditions while it can be easily dissociated at neutral or higher pH values, whereby the polysaccharide may improve stability and viability of lactic acid bacteria under acidic conditions.

Examples of products prepared according to the present double-coating process will be specifically described below.

Example 1

For *Lactobacillus acidophilus* CBT-LH powders which are double-coated, the protein aqueous solution was prepared by suspending 4 kg of skim milk and 2 kg of isolated soybean proteins in 100 kg water and added was an enzyme solution, which was prepared by dissolving 1.02 g of proteolytic enzyme (Protease-N available from Amano Corp.) in 100 ml water, to the protein solution at 55° C. and primary pH value 7.0. Hydrolysis reaction was allowed until the pH value decreases to 6.0 within an enzyme-treating equipment with a low speed stirrer, a thermostat and a pH control device.

After hydrolysis, added and dissolved were 5 kg glucose, 1 kg concentrated meat extract, 0.5 kg yeast extract, 50 g dipotassium phosphate, 50 g ammonium citrate, 50 g sodium acetate, 10 g magnesium sulfate and 10 g manganese sulfate to the solution. This prepared solution was fed into a 200 L anaerobic fermenter and sterilized at 121° C. for 15 minutes.

Afterward, the 2 L starter of *Lactobacillus acidophilus* CBT-LH was cultivated for 12 hours while maintaining a pH level of 6.0 with ammonia. Then, the bacteria cultures and residual protein were precipitated and concentrated after the solution was fed into a continuous centrifuge at a flow rate of 60 L/Hr.

Separately, 10 L of cryoprotectant aqueous solution containing 1 kg trehalose, 1 kg mannitol and 1 kg malto-dextrin was prepared and sterilized under pressure. In addition, 3 L polysaccharide aqueous solution was prepared by dissolving 10 g xantan gum, 10 g cellulose and 10 g levan, followed by sterilizing of the solution under pressure.

The concentrated bacteria cultures were introduced into a mixture of the cryoprotectant and the polysaccharide solution prepared as described above, then fed into a stirrer to form a homogenized solution stirring at 5,000 RPM. This homogenized solution was frozen rapidly to −55° C. and lyophilized at a temperature ranging of 0 to 40° C.

During the centrifugal precipitation process, it was observed that the water-semisoluble residual protein components enclosed the bacteria cells while the water-soluble peptide components were deposited on the cellular walls of the bacteria cells thereby coating the cultures with protein. On the other hand, the polysaccharide components allowed the bacteria cultures to form the bacteria culture group having very dense structures.

It was found that the double-coated lactic acid bacteria produced using protein and the composition of xantan gum, cellulose and levan showed improved stability in the acceleration test, acid-resistance and bile-resistance as compared to the non-coated lactic acid bacteria. Results of the above test are shown in Table 1.

TABLE 1

Results for acid-resistance, bile-resistance and acceleration tests for the double-coated *Lactobacillus acidophilus* CBT-LH

| Acid-resistance test (in artificial gastric juice at pH 2.1) | | | Bile-resistance test (in 0.5% Oxgall solution) | | | Acceleration test (40° C., 70% relative humidity) | | |
|---|---|---|---|---|---|---|---|---|
| Exposure time (min) | Test material (cfu/g) | Control (cfu/g) | Exposure time (min) | Test material (cfu/g) | Control (cfu/g) | Time elapsed (day) | Test material (cfu/g) | Control (cfu/g) |
| 0 | $3.4 \times 10^{11}$ | $3.3 \times 10^{11}$ | 0 | $3.5 \times 10^{11}$ | $3.4 \times 10^{11}$ | 0 | $3.1 \times 10^{11}$ | $3.2 \times 10^{11}$ |
| 30 | $3.2 \times 10^{11}$ | $2.3 \times 10^{11}$ | 30 | $3.3 \times 10^{11}$ | $2.1 \times 10^{11}$ | 10 | $2.9 \times 10^{11}$ | $1.1 \times 10^{11}$ |
| 60 | $3.1 \times 10^{11}$ | $1.5 \times 10^{9}$ | 60 | $3.2 \times 10^{11}$ | $1.4 \times 10^{11}$ | 20 | $2.6 \times 10^{11}$ | $8.9 \times 10^{10}$ |
| 90 | $3.1 \times 10^{11}$ | $1.2 \times 10^{11}$ | 90 | $3.0 \times 10^{11}$ | $1.1 \times 10^{11}$ | 30 | $2.5 \times 10^{11}$ | $1.0 \times 10^{11}$ |
| 120 | $2.9 \times 10^{11}$ | $9.3 \times 10^{10}$ | 120 | $2.9 \times 10^{11}$ | $9.9 \times 10^{10}$ | 40 | $2.0 \times 10^{11}$ | $9.8 \times 10^{9}$ |
| Survival rate after 120 mins (%) | 85.3 | 28.2 | Survival rate after 120 mins (%) | 82.9 | 29.1 | Survival rate after 40 days (%) | 65.5 | 3.1 |

Example 2

For *Streptococcus thermophilus* CBT-ST powders which are double-coated, the protein aqueous solution was prepared by suspending 6 kg of skim milk in 100 kg water and to it was added an enzyme solution, which was prepared by dissolving 6 g of proteolytic enzyme (Protease-N available from Amano Corp.) in 100 ml water, to the protein solution at 55° C. and primary pH 7.0. Hydrolysis reaction was allowed until the pH value decreased to 6.2 within an enzyme-treating equipment with a low speed stirrer, a thermostat and a pH control device.

After hydrolysis, added and dissolved were 4 kg glucose, 0.5 kg concentrated extract concentrate, 0.5 kg yeast extract, 50 g dipotassium phosphate, 50 g ammonium citrate, 50 g sodium acetate, 20 g magnesium sulfate and 5 g manganese sulfate to the solution. This prepared solution was fed into a 200 L anaerobic fermenter and sterilized at 121° C. for 15 minutes.

Afterward, the 2 L starter of *Streptococcus thermophilus* CBT-ST was cultivated for 12 hours while maintaining a pH level of 6.0 with ammonia. Then, the bacteria cultures and residual protein were precipitated and concentrated after the fermented solution was fed into a continuous centrifuge at a flow rate of 60 L/Hr.

Separately, 10 L of cryoprotectant aqueous solution containing 0.5 kg trehalose, 0.5 kg mannitol and 0.5 kg maltodextrin and 1.5 kg skim milk was prepared and sterilized under pressure. In addition, 3 L of polysaccharide aqueous solution was prepared by dissolving 15 g xantan gum and 15 g cellulose, followed by sterilization of the solution under pressure.

The concentrated bacteria cultures were introduced into a mixture of the cryoprotectant solution and the polysaccharide solution prepared as described above, then fed into a stirrer to form a homogenized solution stirring at 5,000 RPM. This homogenized solution was frozen rapidly to −55° C. and lyophilized at a temperature ranging of 0 to 40° C.

It was found that the double-coated lactic acid bacteria, produced by protein-coating using skim milk and polysaccharide-coating using xantan gum and cellulose, showed improved stability in the acceleration test, acid-resistance and bile-resistance as compared to the non-coated lactic acid bacteria. Results of the above test are shown in Table 2.

TABLE 2

Results for acid-resistance, bile-resistance and acceleration tests for double-coated *Streptococcus thermophilus* CBT-ST

| Acid-resistance test (in artificial gastric juice at pH 2.1) | | | Bile-resistance test (in 0.5% Oxgall solution) | | | Acceleration test (40° C., 70% relative humidity) | | |
|---|---|---|---|---|---|---|---|---|
| Exposure time (min) | Test material (cfu/g) | Control (cfu/g) | Exposure time (min) | Test material (cfu/g) | Control (cfu/g) | Time elapsed (day) | Test material (cfu/g) | Control (cfu/g) |
| 0 | $2.0 \times 10^{11}$ | $2.2 \times 10^{11}$ | 0 | $2.7 \times 10^{11}$ | $2.9 \times 10^{11}$ | 0 | $2.6 \times 10^{11}$ | $2.7 \times 10^{11}$ |
| 30 | $1.9 \times 10^{11}$ | $1.7 \times 10^{11}$ | 30 | $2.7 \times 10^{11}$ | $2.3 \times 10^{11}$ | 10 | $2.5 \times 10^{11}$ | $1.3 \times 10^{11}$ |
| 60 | $1.8 \times 10^{11}$ | $1.2 \times 10^{9}$ | 60 | $2.5 \times 10^{11}$ | $1.9 \times 10^{11}$ | 20 | $2.5 \times 10^{11}$ | $9.7 \times 10^{10}$ |
| 90 | $1.8 \times 10^{11}$ | $9.5 \times 10^{10}$ | 90 | $2.4 \times 10^{11}$ | $1.5 \times 10^{11}$ | 30 | $2.4 \times 10^{11}$ | $8.6 \times 10^{10}$ |
| 120 | $1.8 \times 10^{11}$ | $8.4 \times 10^{10}$ | 120 | $2.4 \times 10^{11}$ | $9.2 \times 10^{10}$ | 40 | $2.2 \times 10^{11}$ | $5.1 \times 10^{10}$ |
| Survival rate after 120 mins (%) | 90.0 | 38.2 | Survival rate after 120 mins (%) | 88.9 | 31.7 | Survival rate after 40 days (%) | 84.6 | 18.9 |

Example 3

For *Bifidobacterium longum* CBT-BG powders which are double-coated, the protein aqueous solution was prepared by suspending 2 kg of isolated soybean protein in 100 kg water and added was an enzyme solution, which was prepared by dissolving 5.4 g of proteolytic enzyme (Protease-N available from Amano Corp.) in 100 ml water, to the protein solution at 55° C. and primary pH value 7.0. Hydrolysis reaction was allowed until the pH value decreased to 6.2 within an enzyme-treating equipment with a low speed stirrer, a thermostat and a pH control device.

After hydrolysis, added and dissolved were 4 kg glucose, 0.5 kg meat extract concentrate, 0.5 kg yeast extract, 1 kg casein peptone, 50 g dipotassium phosphate, 50 g potassium phosphate, 10 g magnesium sulfate, 1 g sodium chloride, and 10 g manganese sulfate into the solution. This prepared solution was fed into a 200 L anaerobic fermenter and sterilized at 121° C. for 15 minutes.

Afterward, the 2 L starter of *Bifidobacterium longum* CBT-BG was cultivated for 15 hours while maintaining a pH level of 6.0 with ammonia. The bacteria cultures and residual protein were precipitated and concentrated after the fermented solution was fed into a continuous centrifuge at a flow rate of 60 L/Hr.

The concentrated bacteria culture was introduced into the 10 L of cryoprotectant aqueous solution, containing 0.5 kg trehalose, 0.5 kg mannitol and 0.5 kg malto-dextrin and 1.5 kg skim milk, and mixed homogeneously using a stirrer at 5,000 RPM. This homogenized solution was frozen rapidly to −55° C. and lyophilized at a temperature ranging of 0 to 40° C.

10 g of frozen dried bacteria culture powder was introduced into a polysaccharide solution prepared by dissolving 15 g xantan gum and 15 g cellulose into 3 L of water and mixed homogeneously using stirrer at 5,000 RPM, followed by freezing to −55° C. and lyophilizing under the condition ranging of 0 to 40° C.

It was found that the double-coated lactic acid bacteria, produced by protein-coating using isolated soybean protein and polysaccharide-coating using a combination of xantan gum and cellulose, showed improved stability in the acceleration test, acid-resistance and bile-resistance as compared to the non-coated lactic acid bacteria. Results of the above test are shown in Table 3.

requiring no additional equipment and apparatus in the process for preparing the above double-coated lactic acid bacteria.

The present invention is also applicable to both concentrated bacterial cultures before drying and dried cultures thereby achieving improved flexibility and compatibility of the production process. In particular, the present invention has enhanced the recovery rate of the lactic acid bacteria powders because of a superior survival rate of the bacteria cultures ranging of 50-90%, which improves productivity.

The lactic acid bacteria powders produced by the process according to the present invention show noticeably improved heat-resistance, acid-resistance, bile-resistance and storage stability, as well as excellent viability within the intestines to exhibit superior physiological functions inherent to lactic acid bacteria, thereby having maximum efficiency in using the same.

What is claimed is:

1. A method of preparing double-coated lactic acid bacteria, the method comprising:

providing a protein aqueous solution comprising either or both of skim milk and isolated soybean protein as a protein component;

adding a proteolytic enzyme to the protein aqueous solution, which causes partial hydrolysis of the protein component in the protein aqueous solution to provide a hydrolyzed product comprising water-soluble peptides and water semi-soluble peptides;

cultivating lactic acid bacteria in a fermentation solution comprising the hydrolyzed product, wherein at least part of the water-soluble peptides from the hydrolyzed product are consumed by the lactic acid bacteria, wherein cultivating provides a liquid mixture comprising the lactic acid bacteria, the water-soluble peptides and the water-semisoluble peptides;

TABLE 3

Results for acid-resistance, bile-resistance and acceleration tests for double-coated *Bifidobacterium longum* CBT-BG

| Acid-resistance test (in artificial gastric juice at pH 2.1) | | | Bile-resistance test (in 0.5% Oxgall solution) | | | Acceleration test (40° C., 70% relative humidity) | | |
|---|---|---|---|---|---|---|---|---|
| Exposure time (min) | Test material (cfu/g) | Control (cfu/g) | Exposure time (min) | Test material (cfu/g) | Control (cfu/g) | Time elapsed (day) | Test material (cfu/g) | Control (cfu/g) |
| 0 | $4.0 \times 10^{11}$ | $3.8 \times 10^{11}$ | 0 | $3.6 \times 10^{11}$ | $3.6 \times 10^{11}$ | 0 | $3.6 \times 10^{11}$ | $4.0 \times 10^{11}$ |
| 30 | $3.9 \times 10^{11}$ | $2.3 \times 10^{11}$ | 30 | $3.5 \times 10^{11}$ | $2.6 \times 10^{11}$ | 10 | $3.3 \times 10^{11}$ | $1.1 \times 10^{11}$ |
| 60 | $3.8 \times 10^{11}$ | $2.1 \times 10^{11}$ | 60 | $3.4 \times 10^{11}$ | $2.3 \times 10^{11}$ | 20 | $2.9 \times 10^{11}$ | $9.3 \times 10^{10}$ |
| 90 | $3.8 \times 10^{11}$ | $1.3 \times 10^{10}$ | 90 | $3.2 \times 10^{11}$ | $1.9 \times 10^{10}$ | 30 | $2.7 \times 10^{11}$ | $3.7 \times 10^{10}$ |
| 120 | $3.5 \times 10^{11}$ | $9.9 \times 10^{10}$ | 120 | $3.0 \times 10^{11}$ | $9.8 \times 10^{10}$ | 40 | $2.3 \times 10^{11}$ | $1.4 \times 10^{10}$ |
| Survival rate after 120 mins (%) | 87.5 | 26.1 | Survival rate after 120 mins (%) | 81.3 | 27.2 | Survival rate after 40 days (%) | 63.9 | 3.5 |

As illustrated above, it is shown that the double-coated lactic acid bacteria powders prepared by the method according to the present invention have advantages such as excellent storage stability, acid-resistance, bile-resistance and heat-resistance, as compared to non-coated or primary-coated lactic acid bacteria.

The present invention is applicable in combination with many kinds of cryoprotectants and stabilizers depending on the properties of the used bacteria and can provide double-coated lactic acid bacteria through homogenization in an aqueous solution state and lyophilization process thereby centrifuging the liquid mixture to deposit the water-semisoluble peptides along with the lactic acid bacteria such that deposited water-semisoluble peptides enclose lactic acid bacteria to provide peptide-coated lactic acid bacteria, collecting, from the centrifugation result, the peptide-coated lactic acid bacteria, mixing, in an aqueous solution, the collected peptide-coated lactic acid bacteria with a polysaccharide and a cryoprotectant to provide a homogenized aqueous mixture comprising the peptide-coated lactic acid bacteria, the polysaccharide and the cryoprotectant, freezing the homogenized aqueous mixture to provide a frozen homogenized mixture in which the peptide-coated lactic acid bacteria are enclosed in a polysaccharide coating, and lyophilizing the frozen homogenized mixture, thereby forming double-coated lactic acid bacteria coated with the water-semisoluble peptides and further with the polysaccharide.

2. The method of claim 1, wherein lyophilizing is performed at a temperature ranging from 0° C. to 40° C.

3. The method of claim 1, wherein the polysaccharide is selected from the group consisting of xanthan gum, cellulose, levan and mixtures of the foregoing.

4. The method of claim 1, wherein the lactic acid bacteria are selected from the group consisting of *Lactobacillus acidophilus, Streptococcus thermophilus*, and *Bifidobacterium longum*.

5. The method of claim 1, further comprising:
lyophilizing the peptide-coated lactic acid bacteria prior to mixing with the polysaccharide.

6. The method of claim 1, wherein the cryoprotectant is selected from the group consisting of trehalose, malto-dextrin, mannitol, skim milk and mixtures of the foregoing.

7. The method of claim 1, wherein in the step of freezing, the homogenized aqueous mixture is chilled to a temperature up to −55° C.

8. The method of claim 1, wherein mixing with the polysaccharide comprises stirring the aqueous solution comprising peptide-coated lactic acid bacteria with the polysaccharide and the cryoprotectant at 5,000 RPM.

9. The method of claim 1, wherein centrifuging for depositing the water-semisoluble peptides along with the lactic acid bacteria is conducted using a high speed centrifuge at 15,000 RPM or higher.

10. The method of claim 1, wherein the double-coated lactic acid bacteria has a survival rate of 85.3% or higher after subjecting to an acidic juice at pH 2.1 for 120 minutes.

11. The method of claim 1, wherein the double-coated lactic acid bacteria has a survival rate of 81.3% or higher after subjecting to an Oxgall solution 0.5% for 120 minutes.

12. The method of claim 1, wherein in the step of mixing, the polysaccharide and the cryoprotectant are added to the collected peptided-coated lactic acid in the form of a polysaccharide aqueous solution and a cryoprotectant aqueous solution, respectively.

* * * * *